United States Patent [19]

Sheldrake et al.

[11] Patent Number: 5,646,286
[45] Date of Patent: Jul. 8, 1997

[54] PALLADIUM CATALYZED VINYLIC SUBSTITUTION REACTIONS WITH 2-SUBSTITUTED-PYRIDINES

[75] Inventors: Peter William Sheldrake, Tunbridge Wells; Laurence Charles Powling, Maidstone; Peter William Bickle, Tunbridge Wells, all of England

[73] Assignee: SmithKline Beecham plc, England

[21] Appl. No.: 452,200

[22] Filed: May 26, 1995

Related U.S. Application Data

[63] Continuation of PCT/EP94/02028, Jun. 20, 1994, published as WO95/00487, Jan. 5, 1995.

[51] Int. Cl.⁶ .................. C07D 213/63; C07D 213/66; C07D 213/65
[52] U.S. Cl. .................. 546/301; 546/300; 546/303
[58] Field of Search .................. 546/300, 301, 546/303

[56] References Cited

PUBLICATIONS

Daines et al., Journal of Medicinal Chemistry, vol. 36, No. 18, pp. 2703–2705, Sep. 1993.
Daines et al., Journal of Medicinal Chemistry, vol. 37, No. 20, pp. 3327–3336, Apr. 1994.
Chambers et al., Chemical Abstracts, vol. 119, No. 13 Abst. No. 139, 113h, Sep. 27, 1993.
Daines et al., Chemical Abstracts, vol. 120, No.No. 19, Abst. No. 244, 688t, May 1994

*Primary Examiner*—Alan L. Rotman
*Attorney, Agent, or Firm*—James M. Kanagy; Stephen Venetianer; Edward T. Lentz

[57] ABSTRACT

This invention involves a coupling reaction involving an organo-metallic catalyst, preferably a palladium catalyst involving reacting 2-halo-3-hydroxy-6-hydroxymethylpyridine, acrylic acid or its alkali metal salt and benzyl or a phenylalkyl derivative in presence of a dipolar aprotic solvent producing none other than the expected 2-propenoate-3-benzyl or phenylalkylether-6-hydroxymethyl-pyridine product. Said products are converted into medicaments useful for treating psoriasis.

12 Claims, No Drawings

PALLADIUM CATALYZED VINYLIC SUBSTITUTION REACTIONS WITH 2-SUBSTITUTED-PYRIDINES

CROSS-REFERENCE

This application is a continuation of PCT/EP 94/02028 Jun. 20, 1994, published as WO95/00487 on Jan. 5, 1995.

The present invention relates to an improved process for the preparation of substituted pyridine derivatives. Substituted pyridine derivatives are disclosed in WO93/06085 as medicaments being useful for the treatment of various diseases such as psoriasis.

Various processes for the preparation of these medicaments are also disclosed in WO93/06085. In particular, 2-(trans-2-carboxymethylethenyl)-3-[8-(4-methoxyphenyl) octyloxy]-6-hydroxymethyl pyridine, that is to say, the compound of the following structure:

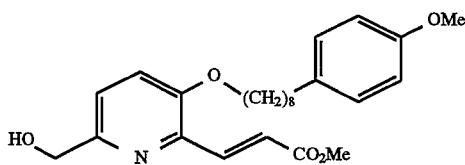

is disclosed as an important intermediate compound. However, the known procedure for the preparation of this type of compound is not ideally suited to large scale application. The object of the present invention is to provide an alternative process for the preparation of such intermediates which is suitable for large scale commercial use.

The present invention therefore provides, in a first aspect, a process for the preparation of a compound of formula (I) or a salt or N-oxide thereof:

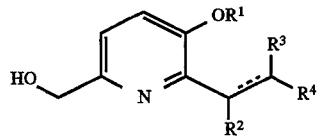

in which $R^1$ is hydrogen, benzyl or a group of formula (A):

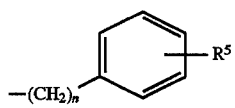

in which n is 1 to 20; and $R^5$ is hydrogen, $C_{1-6}$alkyl, $C_{1-6}$alkoxy or trifluoromethyl; $R^2$ and $R^3$ are independently hydrogen or $C_{1-6}$alkyl; $R^4$ is cyano or $CO_2R^6$ where $R^6$ is hydrogen or $C_{1-6}$alkyl; and the dotted line represents an optional double bond; which process comprises coupling a compound of formula (II):

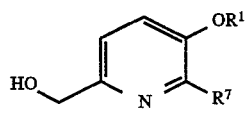

in which $R^1$ is as defined in formula (I) and $R^7$ is a leaving group, with a compound of formula (III) or a salt thereof:

in which $R^2$, $R^3$ and $R^4$ are as defined in formula (I) in the presence of an organometallic catalyst, and optionally thereafter:

converting the resulting compound of formula (I) into a further compound of formula (I)

forming a salt or N-oxide.

Suitable organometallic catalysts include, for example, palladium catalysts. Those skilled in the art will appreciate that palladium catalysts can, if desired, be formed in situ. The processes of the invention can be carded out using pre-prepared catalysts or catalysts formed in situ. Preferred catalysts are palladium (II) catalysts such as $Pd(OAc)_2$, $Pd(OAc)_2/(o-tol)_3P$, $Pd(OAc)_2/Ph_3P$, $Pd(OAc)_2/tri(2-furyl)$ phosphine, $(Ph_3P)_2PdCl_2$ and $PdCl_2/Ph_3P$.

Preferably $R^1$ is a group of formula (A) where $R^5$ is $C_{1-6}$alkoxy, for example methoxy. When $R^1$ is a group of formula (A), n is Suitably 1 m 20, preferably n is 2 to 8.

Suitably $R^2$ and $R^3$ are hydrogen or $C_{1-6}$alkyl, preferably $R^2$ and $R^3$ are both hydrogen.

Suitably $R^4$ is cyano or $CO_2R^6$ where $R^6$ is hydrogen or $C_{1-6}$alkyl, preferably $R^4$ is $CO_2R^6$ where $R^6$ is $C_{1-6}$alkyl such as methyl or butyl.

Suitably $R^7$ is a leaving group such as halogen, OTf or $OSO_2Ar$ where Ar is an optionally substituted aryl group. Suitable substituents include $C_{1-6}$alkyl, for example methyl. Preferably $R^7$ is halogen, in particular bromo or iodo.

Preferred compounds of formula (I) which can be prepared using the above process include: n-butyl 3-{6-hydroxymethyl-3-[8(4-methoxyphenyl)octyloxy]pyridin-2-yl} propenoate, methyl 3-{6-hydroxymethyl-3-[8(4-methoxyphenyl)octyloxy]pyridin-2-yl} propenoate, methyl 3-{6-hydroxymethyl-3-(phenylethyloxy)pyridin-2-yl} propenoate, t-butyl 3-[6-hydroxymethyl-3-[8(4-methoxyphenyl)<octyloxy]pyridin-2-yl} propenoate, 3-{6-hydroxymethyl-3-[8(4-methoxyphenyl)octyloxy]pyridin-2-yl} propenoic acid, n-butyl 3-{6-hydroxymethyl-3-(phenylethyloxy)pyridin-2-yl} propenoate, ethyl (3-hydroxy-6-methylpyridin-2-yl)propenoate, ethyl 3-{3-hydroxy-6-hydroxymethylpyridin2-yl} propenoate, ethyl (3-benzyloxy-6-hydroxymethylpyridin-2-yl)propenoate, n-butyl (3-benzyloxy-6-hydroxymethylpyridin-2-yl) propenoate, and methyl (3-benzyloxy-6-hydroxymethylpyridin-2-yl)propenoate, and salts and N-oxides thereof.

The coupling reaction is carried out in a suitable solvent, preferably at elevated temperature. Preferably the coupling reaction is carried out in DMF, in particular aqueous DMF, at a temperature of about 80° to about 160° C., preferably at about 120° C.

The term 'salts' in relation to compounds of formula (III) refers to carboxylate salts of compounds of formula (III), in which $R^4$ is $CO_2^\ominus M^\oplus$ where M is a metal ion such as sodium or potassium. Examples of such compounds include potassium acrylate.

Salts of compounds of formula (I) can be prepared by treatment with an inorganic or organic acid, or when $R^4$ is $CO_2H$, by treatment with an inorganic or organic base. N-oxides of the pyridyl nitrogen can be prepared using standard techniques.

Compounds of formulae (II) and (III) are commercially available or can be prepared using standard procedures well known to those skilled in the art.

For example, compounds of formula (II) in which $R^1$ is a group of formula (A) can be prepared by reaction of a compound of formula (II) in which $R^1$ is hydrogen with a compound of formula (IV):

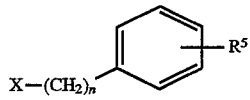
(IV)

in which n and $R^5$ are as defined in formula (II) and X is a leaving group.

Suitably leaving groups X include, for example, halo, $C_{1-6}$alkylSO$_2$ such as methanesulphonyl or ArSO$_2$ where Ar is optionally substituted phenyl, for example p-toluenesulphonyl. Preferably X is halo or p-toluenesulphonyl. Compounds of formula (II) in which $R^1$ is hydrogen can be reacted with compounds of formula (IV) in the presence of a suitable base in an inert solvent, preferably at elevated temperature. For example, the reaction can be carried out using potassium or sodium carbonate in DMF at elevated temperatures Compounds of formula (I) can be converted into further compounds of formula (I) using standard procedures. For example a compound of formula (I) in which $R^1$ is benzyl may be converted into a compound of formula (I) in which $R^1$ is hydrogen by hydrogenation. A compound of formula (I) in which $R^1$ is hydrogen can be reacted with a compound of formula (IV) under conditions described above to give a compound of formula (I) in which $R^1$ is a group of formula (A). Compounds of formula (I) in which $R^4$ is $CO_2R^6$ where $R^6$ is $C_{1-6}$alkyl can be converted into compounds of formula (I) in which $R^4$ is $CO_2H$ using standard ester hydrolysis procedures. Compounds of formula (I) in which the dotted line represents a double bond, that is to say forming a group $CR^2=CR^3-R^4$, can be converted to the corresponding saturated compounds having the group $CHR^2-CHR^3-R^4$ by hydrogenation.

As mentioned above, compounds of formula (I) are intermediates for the preparation of medicaments. In a further aspect, the present invention therefore provides a process for the preparation of a compound of formula (IA) or a salt or N-oxide thereof:

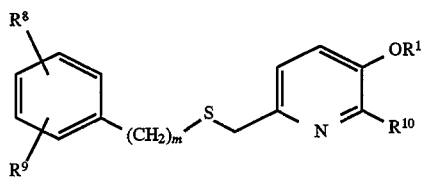
(IA)

in which:

$R^1$ is hydrogen, benzyl or a group of formula (A):

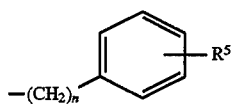
(A)

where n is 1 to 20 and $R^5$ is hydrogen, $C_{1-6}$alkyl, $C_{1-6}$alkoxy or trifluoromethyl; m is 0 to 5; $R^8$ and $R^9$ are independently hydrogen, halogen, $CO_2H$, $C_{1-6}$alkyl or $C_{1-6}$alkoxy; and $R^{10}$ is a group $CR^2=CR^3-R^4$ or $CHR^2-CHR^3-R^4$ where $R^2$ and $R^3$ are independently hydrogen or $C_{1-6}$alkyl and $R^4$ is cyano or $CO_2R^6$ where $R^6$ is hydrogen or $C_{1-6}$alkyl, which process comprises: coupling a compound of formula (II):

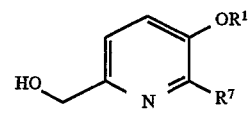
(II)

in which $R^1$ is as defined in formula (IA) and $R^7$ is a leaving group with a compound of formula (III) or a salt thereof:

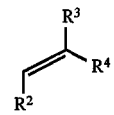
(III)

in which $R^2$, $R^3$ and $R^4$ are as defined in formula (IA) in the presence of an organometallic catalyst, to give a compound of formula (I):

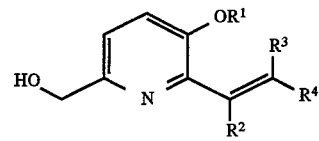
(I)

in which $R^1$, $R^2$, $R^3$ and $R^4$ are as defined in formula (IA), and thereafter:

converting the compound of formula (I) into a compound of formula (IA)

optionally converting a compound of formula (IA) into another compound of formula (IA)

optionally forming a pharmaceutically acceptable salt or N-oxide.

Preferred substituents and conditions for the preparation of compounds of formula (I) are the same as those indicated above.

A compound compound of formula (I) can be convened into a compound of formula (IA) by initially converting the compound of formula (I) into a compound of formula (V):

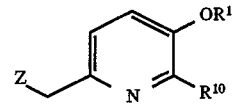
(V)

in which $R^1$ and $R^{10}$ are as defined in formula (LA) and Z is a leaving group, and thereafter reacting the compound of formula (V) with a compound of formula (VI)

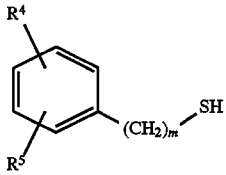
(VI)

in which $R^4$, $R^5$ and m are as defined in formula (IA).

In compounds of formula (V) Z is a suitable leaving group, for example those leaving groups defined above for X Preferably Z is halo, in particular chloro.

Compounds of formula (V) can be coupled with compounds of formula C/I) under standard conditions, for example in the presence of a base such as potassium carbonate in an inert solvent or aqueous sodium hydroxide in an inert solvent such as THF/methanol.

Compounds of formula (V) and (VI) can be prepared using standard procedures. For example a compound of formula (V) in which Z is halo and $R^{10}$ is $CR^2=CR^3-R^4$ can be prepared by treating a compound of formula (I) with a halogenating agent such as thionyl chloride. When $R^{10}$ is a group $CR^2=CR^3—R^4$ this may first be reduced to a group $CHR^{2-}—R^3—R^4$ by hydrogenation in the presence of a suitable catalyst, or by treating with with magnesium in methanol, preferably before introduction of the leaving group Z and subsequent coupling Compounds of formula (IA) can be convened into other compounds of formula (IA) using standard chemistry. For example a compound of formula (IA) in which $R^{10}$ is $CR^2=CR^3—R^4$ can be convened into a compound of formula (IA) in which $R^{10}$ is $CHR^2—CHR^3—R^4$ by hydrogenation. Compounds of formula (IA) in which $R^1$ is hydrogen or benzyl can be convened to compounds of formula (IA) in which $R^1$ is a group of formula (A) by reaction with a compound of formula (IV) under conditions described above.

It will be appreciated that for use in medicine a salt of a compound (IA) should be pharmaceutically acceptable. Examples of pharmaceutically aeceptable salts include inorganic and organic acid addition salts such as hydrochloride, hydrobromide, sulphate, phosphate, acetate, fumarate, maleate, citrate, lactate, tartrate, oxalate, methanesulphonate or similar pharmaceutically acceptable inorganic or organic acid addition salts.

Other non-pharmaceutically acceptable salts may be used for example in the isolation of intermediate or final products and are included within the scope of this invention. When $R^4$ is $CO_2H$, salts can be prepared by treatment with an inorganic or organic base. For compounds which do not possess a sulphur group, N-oxides of the pyridyl nitrogen can be prepared using standard techniques.

Particularly preferred compounds of formula (IA) which can be prepared using the above process include 3[2-thia-3-[2-(E-2-carboxyethenyl-3-[8-(4-methoxyphenyl) octyloxy]-6-pyridyl]propyl]benzoic acid, [[1-thia-2-[6-(2-earboxyethyl)-5-phenylethyloxy-2-pyridyl]]ethyl]-2,6-dichlorobenzene and [[1-thia-2-[6-(E-2-carboxyethenyl)-5-phenylethyloxy-2-pyridyl]]ethyl]-2,6-dichlorobenzene or pharmaceutically acceptable salts or N-oxides thereof.

Certain compounds of formulae (II) and (V) are themselves believed to be novel and form a further aspect of the invention.

The following examples serve to illustrate the invention.

EXAMPLE 1 n-Butyl 3-{6-hydroxymethyl-3-[8(4-methoxyphenyl) octyloxy] pyridin-2-yl} propenoate (a) 2-Bromo-3-hydroxypyridine[1]

Bromine (2.74 ml, 8.49 g, 5.31 mmol) was added to 10% sodium hydroxide solution (50 ml) at 5°–10° C. This hypobromite solution was added over 20 min to a solution of 3-hydroxypyridine (5.0 g, 52.6 mmol) in 10% sodium hydroxide (50 ml). The mixture was stirred an additional 30 min. Acetic acid was added to bring the pH of the solution to between pH 6 and pH 7. The mixture was cooled to 5° C. for 1 h and the product filtered off. It was washed with water and dried in vacuum at 85° C. to give the product (6.22 g, 67%). Reference: 1) GJ Clark & L W Deedy, Australian J Chem, (1981), 34, 927

(b) 1-Bromo-8-chlorooctane 1,8-Octanediol (72 g, 0.5 mmol), toluene (1 L) and 48% hydrobromic acid (110 g, 0.65 mol) were heated to reflux and water azeotropically removed. The solution was cooled to 60° C., extracted with 10% hydrochloric acid (3×300 ml) and redtied by azeotropic distillation. DMF (2.5 ml) was added, the mixture heated to 75° C. and thionyl chloride (55.6 g, 0.47 mmol) added over 10 min such that this temperature was maintained. The temperature was raised to 85°–90° C. for 1 h and the reaction checked by GC for unreacted 1-bromooctan-8-ol (in this case found to be 1.9% by PAR). The mixture was cooled to 80° C. and washed successively with 10% sodium hydroxide solution (2×200 ml) and water (2×300 ml, 1×400 ml). Toluene (550 ml) was removed by distillation to leave 259.2 g of solution containing 1-bromo-8-chlorooctane. This was used directly in the reaction with anisylmagnesinm bromide. The yield can be calculated by GC assay against an internal standard or by chlorine analysis. Typically it is in the range 80–85%.

(c) Anisylmagnesium Bromide

Magnesium (36 g, 1.5 mmol), iodine (a few crystals) and THF (1 L) were heated under nitrogen, with stirring, at reflux for 15 min. The mixture was cooled to 20° C., stirring stopped, and 1,2-dibromoethane (2.5 ml) added. After an exothermic reaction was observed (a few min) stirring was restarted which was accompanied by a rise in temperature to 35° C. The mixture was cooled to 20° C. and 4-bromoanisole slowly added over 1 h at 14°–18° C. with cooling. Stirring was continued for 10 min after the addition was complete.

The solution was assayed (HPLC) after an aqueous quench which gave a molarity of 0.88. Alternatively it can be tinted against sec-butanol in xylene using 1,10-phenanthroline as indicator.

(d) 1-Chloro-8-(4-methoxyphenyl)-octane

Bromochlorooctane in toluene (256 g containing approx 95.3 g, 0.42 mol), lithium tetrachlorocuprate in THF (33 ml of 1 mmol solution) and THF (46 ml) were heated to reflux (98° C.) under nitrogen. Anisylmagnesium bromide solution (0.75 L) was added over 10 min such that a vigorous reflux was maintained. Reflux was continued (78° C., 1 h) until no bromochlorooctane remained by GC analysis. The mixture was cooled to 20° C. and 10% ammonium chloride solution (0.5 L) added (cooling required). After phase separation the organic phase was further washed with ammonium chloride solution (0.5L) and saturated sodium chloride solution (3×0.5 L). The organic solution was dried over magnesium sulphate, filtered, and the solvent removed under reduced pressure to leave 124.9 g of crude product. This was distilled (178°–205° C., 3 mb) to give 72.1 g containing 59.7 g on assay. This represents a yield of 46.4% from octanediol.

(e) 2-Bromo-3-hydroxy-6-hydroxymethylpyridine

Potassium hydroxide (85% assay, 113.8 g, 1.73 mol) was dissolved in distilled water (750 ml) and to the solution was added 2-bromo-3-hydroxypyridine (300 g, 1.72 mol), ethylenediaminetetraacetic acid sodium salt (2 mmol %, 13.1 g, 0.034 mmol) and formalin (3741% w/v 470 ml, 5.95 mmol). The stirred mixture was heated at 90°–95° C. until the assay (HPLC) of remaining starting material fell below 3% (approx 5 h). The reaction mixture was then cooled to room temperature and glacial acetic acid (103 ml) added and stirred for a further 2h. The precipitated solid was filtered from the mixture and the filtrate saturated with sodium chloride (310 g). The resulting solution was extracted with ethyl acetate (4×280ml). The combined organic extracts were dried and evaporated to dryness keeping the temperature below 85° C. The residue was assayed by HPLC to determine the quantity of contained 2-bromo-3-hydroxy-6-hydroxymethylpyridine. The yield was typically 65%.

The quantifies of materials used in the alkylation reaction are based on the assay.

(f) 2-Bromo-6-hydroxymethyl-3-[8(4-methoxyphenyl) octyloxy]pyridine hydrobromide The crude 2-bromo-3-hydroxy-6-hydroxymethylpyridine (vide supra, 1.12 mol) was dissolved in dimethyl formamide (1150 ml) at 60° C. 1-Chloro-8-(4-anisyl)-octane (342 g, 1.34 mmol) and potassium carbonate (388 g, 2.81 mol) were added. It was found to be important that the potassium carbonate was ground to as fine a powder as possible. The mixture was stirred vigorously and heated to 90°–95° C. until the assay of 2-bromo-3-hydroxy-6-hydroxymethylpyridine (by HPLC) fell below 3% (approx 5 h). The mixture was then cooled to room temperature, poured into water (10 L) and extracted with ethyl acetate (3×670 ml). The combined ethyl acetate extracts were washed with water (2×500 ml) and dried before being evaporated to dryness. The crude reaction product was dissolved in butan-1-ol (2700 ml) and hydrogen bromide gas (120 g) passed through the solution keeping the temperature below 70° C. After allowing the mixture to cool to 10° C. with vigorous stirring the solid product was filtered and washed with ethyl acetate (2×500 ml). The solid product was dried under vacuum at 60° C. for 4 days. Yield 421 g, 75%.

(g) n-Butyl 3-{6-hydroxymethyl-3-[8(4-methoxyphenyl) octyloxy]pyridin-2-yl} propenoate 2-Bromo-6-hydroxymethyl-318(4-methoxyphenyl) octyloxy]pyridine (5.01 g, 11.9 mmol), tetra-n-butylammonium iodide (4.38 g, 11.9 mmol), potassium acetate (3.01 g, 30.7mmol), bis(triphenylphosphine) palladium dichloride (0.33 g, 0.5 mmol) DMF (23 ml), water (1.2 ml) and n-butyl acrylate (3.4 ml, 3.05 g, 23.8 mmol) were placed under nitrogen by repeated evacuation and filling of the flask. The mixture was stirred and heated at 120° C. until starting material was consumed (HPLC), typically 2–8h. The reaction mix was cooled and poured into water (250 ml). The product was extracted into ethyl acetate (3×80 ml) and the combined extracts were washed with water (3×60 ml). The organic layer was dried over sodium sulphate and evaporated. The residue was purified by flash column chromatography to give the product as an oil, 4.17g, 75%.

EXAMPLE 2 n-Butyl 3-{6-hydroxymethyl-3-[8(4-methoxyphenyl) octyloxy]pyridin-2-yl}propenoate hydrochloride To a solution of 6-hydroxymethyl-2-iodo-3-[8(4-methoxyphenyl)octyloxy]pyridine (2.34 g, 5.0 mmol) in DMF (9.5 ml) and water (0.5 ml) were added potassium acetate (1.23 g, 12.5 mmol), palladium acetate (45 mg, 0.2 mmol) and n-butyl acrylate (2.16 ml, 192 g, 15 mmol). The mixture was placed under nitrogen and stirred and heated at 120° C. for 50 min. The mixture was cooled and added to water (60 ml). The product was extracted into ethyl acetate (3×20 ml) and the combined extracts washed with water (10 ml) and 5% sodium chloride solution (2×10 ml). The extracts were dried and evaporated. The residue was taken up in n-butanol (20 ml) and warmed to 50° C. Hydrogen chloride was passed into the solution, which was then cooled m 5° C. The product (as hydrochloride) was filtered, washed with n-butanol and ethyl acetate and dried (1.45 g, 57%). mp 152°–1.54° C.

NMR $\delta$(CDCl$_3$): 0.97 (2H, t, J=7 Hz); 1.1–1.95 (16 H, m); 2.55 (2H, t, J=7 Hz); 3.77 (3H, s); 3.91 (1H, t, J=5 Hz, OH); 4.00 (2H, t, J=7 Hz); 4.2I (2H, t, J=7 Hz); 4.69(2H, d, J=5Hz);6.83 (2H, d, J=7 Hz); 6.95–7.4 (5H, m); 8.0g (1H, d, J=15Hz).

EXAMPLE 3

Methyl 3-{6-hydroxymethyl-3-[8(4-methoxyphenyl) octyloxy]pyridin-2-yl}propenoate Following the procedure outlined in Example 1(g), 2-Bromo-6-hydroxymethyl-3-[8(4-methoxyphenyl) octyloxy]pyridine was treated with an equivalent amount of methyl acrylate to give methyl 3-{6-hydroxymethyl-3-[8(4-methoxyphenyl) octyloxy]pyridin-2-yl} propenoate in similar yield. The methyl ester solidifies on standing.

EXAMPLE 4

Methyl 3-{6-hydroxymethyl-318(4-methoxyphenyl) octyloxy]pyridin-2-yl}propenoate hydrochloride 2-Bromo-6-hydroxymethyl-3-[8(4-methoxyphenyl) octyloxy]pyridine (19.8 g, 46.9 mmol) was dissolved in DMF (90.3 g) and to the solution were added potassium acetate (11.55 g, 118.0 mmol), tetra-n-butylammonium iodide (17.38 g, 47.0 mmol), bis(triphenylphosphine) palladium dichloride (1.32 g, 1.88 mmol) and methyl acrylate (12.20 g, 142.0 mmol). The mixture was placed under nitrogen and stirred and heated at 120° C. for 24 h. The mix was added to water (500 ml). The product was extracted into ethyl acetate (2×200 ml). The combined extracts were washed with water (2×200 ml), dried and evaporated to leave an oil (28.7 g). This residue was taken up in 2-propanol (230 ml) and filtered from insoluble material. The filtrate was treated with a solution of hydrogen chloride in methanol (9% w/w; about 19 ml) to precipitate the product as its hydrochloride (16.88 g, 67%). mp 136°–140° C.

NMR $\delta$ (CDCl$_3$):

1.1–1.7 (10H, m); 1.91 (2H, quin, J=7 Hz); 2.54 (2H t, J=7 Hz); 3.79 (3H, s); 3.84 (3H, s); 5.03 (2H, s); 6.82 (2H, d, J=7 Hz);7.11 (2H, d, J=7 Hz); 7.67(1H, d, J=15 Hz); 7.84 (2H, m); 8.11 (1H, d, J=15 Hz).

EXAMPLE 5 t-Butyl 3-{6-hydroxymethyl-3-[8(4-methoxyphenyl) octyloxy]pyridin-2-yl}propenoate To a solution of 2-bromo-6-hydroxymethyl-[8(4-methoxyphenyl)octyloxy]pyridine (5.00 g, 11.8 mmol) in DMF (22.8 ml) and water (1.2 ml) were added potassium acetate (3.00 g, 30.6 mmol), tetra-n-butylammonium iodide (4.36 g, 11.8 mmol), bis(triphenylphosphine)palladium dichloride (0.33 g, 0.47 mmol) and t-butyl acrylate (6.16 g, 48 mmol). The mixture was placed under nitrogen and stirred and heated at 120° C. for 45 min. The mixture was cooled and added to water (250 ml). The product was extracted into ethyl acetate (2×60 ml). The combined extracts were washed with water (100 ml), 5% sodium chloride solution (2×100 ml), then dried and evaporated. The product was obtained by flash column chromatography using silica and 10% ether in dichloromethane. Yield 4.29 g, 77%.

EXAMPLE 6

3-{6-Hydroxymethyl-3-[8(4-methoxyphenyl)octyloxy] pyridin-2-yl}propenoic Acid a) Using acrylic acid To a solution of 2-bromo-6-hydroxymethyl-[8(4-methoxyphenyl)octyloxy]pyridine (5.00 g, 11.8 mmol) in DMF (22.8 ml) and water (1.2 ml) were added potassium acetate (2.91 g, 29.7 mmol), tetra-n-butyl ammonium iodide (4.37 g, 11.8 mmol), bis(triphenylphosphine)palladium dichloride (0.33 g, 0.47 mmol) and acrylic acid (2.55 g, 35.4 mmol). The mixture was placed under nitrogen and stirred and heated at 120° C. for 5.5 h. The mix was cooled, solids filtered and washed with ethyl acetate (100 ml). The filtrate was washed with water (250 ml, 2×125 ml), dried and evaporated to leave a solid. Pure product was obtained by flash column chromatography (silica, 20% ether in dichloromethane) (3.28 g, 67%).

b) Using potassium acrylate

To a solution of 2-bromo-6-hydroxymethyl-[8(4-methoxyphenyl)octyloxy]pyridine (5.00 g, 11.8 mmol) in DMF (22.8 ml) and water (1.2 ml) were added potassium acetate (2.91 g, 29.7 mmol), tetra-n-butylammonium iodide (4.37 g, 11.8 mmol), triphenylphosphine (0.245 g, 0.94 mmol), palladium chloride (83 mg, 0.47 mmol) and potassium acrylate (3.91 g, 35.4 mmol). The mixture was placed under nitrogen and stirred and heated at 120° C. for 3.3 h. Some potassium acrylate remained undissolved. The mixture was cooled, solids filtered and washed with ethyl acetate (2×60 ml). The filtrate was washed with water (250 ml) and with 5% sodium chloride solution (2×125 ml). The organic layer was dried and evaporated. The pure product was obtained by flash column chromatography (silica, 2.0% ether in dichloromethane) (3.52 g, 72%). mp 112°114° C.

NMR δ(CDCl$_3$): 1.1–1.7 (10H, m); 1.83 (2H, quin, J=7 Hz); 2.62 (2H, t, J=7 Hz); 3.77 (3H, s); 4.00 (2H, t, J=7 Hz); 4.70 (2H, s); 6.80 (2H, d, J=7 Hz); 7.0–7.3 m); 8.17 (1H, d, J=14 Hz).

EXAMPLE 7 n-Butyl 3-{6-hydroxymethyl-3-(phenethyloxy)pyridin-2-yl}propenoate

To a solution of 2-bromo-6-hydroxymethyl-3-phenethyloxypyridine (1.33 g, 4.32mmol) in DMF (4.75 ml) and water (0.25 ml) were added potassium acetate (1.23 g, 5.13 mmol), tetra-n-butyl ammonium iodide (1.89 g, 5.13 mmol), bis(triphenylphosphine)palladium dichloride (0.144 g, 0.205 mmol) and n-butyl acrylate (1.48 ml, 1.31 g, 10.3 mmol)). The mixture was placed under nitrogen and stirred and heated at 120° C. for 21 h. The mixture was cooled and poured into water (60 ml). The product was extracted into ethyl acetate (3×20 ml). The combined extracts were washed with water, dried and evaporated. The residue was purified by flash column chromatography eluting with ether to give the product (1.24 g, 81%). mp (B.HCl) 180°–185° C.

NMR δ (CDCl$_3$): 0.98 (3H, t, J=7 Hz); 1.46 (21-1, sx, J=7 Hz); 1.72 (2H, quin, J=7 Hz); 3.18(2H, t, J=7 Hz); 3.6 (1H, broad t); 4.25 (4H, overlapping t's); 4.70 (2H, broad d); 7.04 (1H, d, J=15 Hz); 7.1–7.4 (7H, m); 8.10 (1H, d, J=15 Hz).

EXAMPLE 8

Ethyl (3-hydroxy-6-methylpyridin-2-yl)propenoate

To a solution of 3-hydroxy-2-iodo-6-methylpyridine (1.175 g, 5.0 mmol) in DMF (9.5 ml) and water (0.5 ml) were added potassium acetate (1.23 g, 12.5 mmol), triphenylphosphine (105 mg, 0.40 mmol), palladium chloride (36 mg, 0.20 mmol) and ethyl acrylate (1.63 ml, 1.50 g, 15.0 mmol). The mixture was placed under nitrogen and heated at 120° C. for 1.5 h. The mixture was cooled, filtered from deposited palladium black, and added to water (100 ml). The product was extracted into ethyl acetate (3×30 ml). The combined extracts were washed with water (2×25 ml) and with brine (25 ml), then dried over sodium sulphate and evaporated. This left a tan solid, the product (951 mg, 91%). mp 192°–195° C. (dec)

NMR δ(d$^6$—DMSO, 40°): 1.15 (3H, t J=7 Hz); 2.38 (3H, s); 3.25 (1H, s, OH); 4.20 (2H, q, J=7 Hz); 6.80(1H, d, J=16 Hz); 7.1–7.2 (2H, m); 7.90 (1H, d, J=16 Hz).

EXAMPLE 9

Ethyl 3-{3-hydroxy-6-hydroxymethylpyridin2-yl}propenoate

To a solution of 3-hydroxy-6-hydroxymethyl-2-iodopyridine (708 mg, 2.82 mmol) in DMF (5.7 ml) and water (0.3 ml) were added potassium acetate (0.74 g, 7.5mmol), triphenylphosphine (63 mg, 0.24 mmol), ethyl amylate (0.98 ml, 0.90g, 9.0 mmol) and palladium acetate (27 mg, 0.12 mmol). The mixture was placed under nitrogen and stirred and heated at 120° C. for 5 h. The mix was cooled and poured into water (50 ml). The product was extracted into ethyl acetate (3×20ml) and the combined extracts were washed with water (2×15 ml) with brine (15 ml), dried and evaporated. The crude product was purified by passage in ethyl acetate through a pad of silica, yielding after evaporation a yellow solid (295 g, 47%). mp (B.HCl) 199°–203° C.

NMR δ (B.HCl) (d$^6$-DMSO, 40°): 1.26 (3H, t, J=7 Hz); 4.23 (2H, q, J=7 Hz); 4.63 (2H, s); 7.10 (1H, d, J=8 Hz); 7.81 (1H, d, J=8 Hz); 7.94 (1H, d, J=16Hz).

EXAMPLE 10

Ethyl (3-benzyloxy-6-hydroxymethylpyridin-2-yl) propenoate a) From 3-benzyloxy-2-bromo-6-hydroxymethylpyridine To a solution of 3-benzyloxy-2-bromo-6-hydroxymethylpyridine (5.00 g, 17.0 mmol) in DMF (32.3 ml) and water (1.7 ml) were added potassium acetate (4.17 g, 42.5 mmol), tetra-n-butylammonium iodide (6.27 g, 17.0 mmol), bis-(triphenylphosphine)palladium dichloride (0.48 g, 0.68 mmol) and ethyl acrylate (5.53 ml, 5.1 g, 51.0 mmol). The mixture was placed under nitrogen and stirred and heated at 120° C. for 5 h. The reaction mix was cooled and poured into water (300 ml). The product was extracted into ethyl acetate (3×50 ml). The combined extracts were washed with water (3×40 ml) and with brine. Anhydrous sodium sulphate and charcoal (0.5 g) were added to the organic solution and stirred for 15 min. The solution was filtered and the filtrate evaporated. The residue was dissolved in toluene (12 ml) at 80° C. and hexane (6 ml) added at the same temperature. The solution was cooled to 0° C. The crystalline product was filtered off, washed with 1:1 toluene: hexane (10 ml) and dried. The yield was 4.20 g, 79%. mp 106°–108° C.

NMR δ(CDCl$_3$):

1.35 (3H, t, J=7 Hz); 3.60 (1H, broad s); 4.26 (2H, q, J=7 Hz); 4.70 (2H, broad s); 5.18 (2N, s); 7.05 (1H, d, J=16 Hz); 7.1–7.45 (7H, m); 8.16 (1H, s, J=16Hz).

b) From 3-benzyloxy-6-hydroxymethyl-2-iodopyridine

To a solution of 3-benzyloxy-6-hydroxymethyl-2-iodopyridine (1.20 g, 3.50 mmol) in DMF (6.4 ml) and water (0.32 ml) were added potassium acetate (0.83 g, 8.5 mmol) palladium acetate (32 mg, 0.14 mmol) and ethyl acrylate (1.1ml, 1.01 g, 10 mmol). The mixture was placed under nitrogen and stirred and heated at 120° C. for 1.25 h. By hplc the solution yield was 62%.

NMR δ(CDCl$_3$): 0.97 (3H, t, J=7 Hz); 1.44 (2H, sx, J=7 Hz); 1.68 (2H, m, J=7 Hz); 3.60(1H, broad t), 4.20 (2H, t, J=7 Hz); 4.67 (2H, broad d); 5.16 (2H, s); 7.04(1H, d, J=16 Hz); 7.1–7.45 (m, 7H); 8.16 (1H, d, J=16 Hz).

EXAMPLE 11 n-Butyl (3-benzyloxy-6-hydroxymethylpyridin-2-yl) propenoate

To a solution of 2-bromo-3-benzyloxy-6-hydroxymethylpyridine (2.94 g, 10.0 mmol) in DMF (19 ml) and water (1 ml) were added potassium acetate (2.45 g, 25.0 mmol), tetra-n-butylammonium iodide (3.69 g, 10.0 mmol), bis(triphenylphosphine)palladium dichloride (281 mg, 0.4 mmol) and n-butyl acrylate (4.31 ml, 3.84 g, 30 mmol). The mixture was placed under nitrogen and stirred and heated at 120° C. for 3 h. The mixture was cooled and poured into water (180 ml). The product was extracted into ethyl acetate (3×30 ml). The combined extracts were washed with water (3×25 ml), dried and evaporated. This residue was purified by flash column chromatography, eluting with a gradient of ethyl acetate in dichloromethane to isolate the product, an oil (2.72 g, 80%).

NMR δ(CDCl$_3$): 0.97 (3H, t, J=7 Hz); 1.44 (2H, sx, J=7 Hz); 1.68 (2H, m, J=7 Hz); 3.60(1H, broad t), 4.20 (2H, t, J=7 Hz); 4.67 (2H, broad d); 5.16 (2H, s); 7.04(1H, d, J=16 Hz); 7.1–7.45 (m, 7H); 8.16 (1H, J=16 Hz).

EXAMPLE 12

Methyl (3-benzyloxy-6-hydroxymethylpyridin-2-yl) propenoate

To a solution of 2-bromo-3-benzyloxy-6-hydroxymethylpyridine (2.94 g, 10 mmol) in DMF (19 ml) and water (1 ml) were added potassium acetate (2.45 g, 10.0 mmol), tetra-n-butylammonium iodide (3.69 g. 10.0 mmol), bis(triphenyl-phosphine)palladium dichloride (281 mg, 0.4 mmol) and methyl acrylate (2.70 ml. 2.58 g, 30 mmol). The mixture was placed under nitrogen and stirred and heated at 120° C. for 5 h. The mixture was cooled and added to water (180 ml). The product was extracted into ethyl acetate (3×30 ml). The combined extracts were washed with water (3×25 ml), dried and evaporated. The residue was purified by flash column chromatography eluting with dichloromethane, then 4:1 dichloromethane:ethyl acetate to give the product (2.516 g, 84%).

NMR δ (CDCl$_3$): 3.80 (3H, s); 4.70 (2H, s); 5.16 (2H, s); 7.05 (1H, d, J=16 Hz); 7.1–7.45 (7H, m); 8.16 (1H, d, J=16 Hz).

EXAMPLE 13 n-Butyl 3-{6-Hydroxymethyl-3-[8(4-methoxyphenyl)octyloxy]pyridin-2-yl}propenoate 2-Bromo-6-hydroxymethyl-3-[8(4-methoxyphenyl) oayloxy]pyridine hydro-bromide (10.0 kg, 19.87 mmol) was added to a solution of sodium hydroxide (0.82 kg, 20.5 mol) in demineralised water (16.4 L), mixed with ethyl acetate (54.7 kg). The mixture was stirred for 15 mln and the phases separated. The aqueous phase was washed with ethyl acetate (6.1 kg). The bulked organic solutions were washed with demineralised water (11.4 L). The mixture was heated to reflux under 'Dean and Stark' conditions until 0.3 L of water had been collected. Solvent (45.0 L) was removed by distillation at atmospheric pressure. Dimethyl formamide (50.0 kg) was added and distillation continued under low vacuum to remove a further 37.0 L of solvent. The mixture was cooled to 20° C. Potassium acetate (4.50 kg, 45.85 mmol) was added, followed by tetra-n-butylammonium iodide (6.75 kg, 18.27 mmol).

Triphenylphosphine (0.4177 kg, 1.59 mol) and palladium dichloride (0.1412 kg, 0.89 mmol) were stirred in dimethylformamide (4.0 kg) to form bis(triphenyl phosphine) palladium dichloride. This mixture was added to the reaction solution followed by n-butyl acrylate (7.02 kg, 54.77 mmol) and demineralised water (2.0 L).

The mixture was heated to 120°–125° C. and stirred at this temperature for 3.75 h under a slight nitrogen pressure (100 mb).

The mixture was cooled to 20° C. and filtered. The filtrate was added to a mixture of demineralised water (386.0 L) and ethyl acetate (41.0 kg). The filter was washed with ethyl acetate (30.5 kg) and the wash added to the solution. The mixture was stirred for 15 min and the phases separated. The aqueous phase was washed with ethyl acetate (28.7 kg). The organic phases were combined and washed with demineralised water (3×22.7 L).

The organic solution was heated to reflux under 'Dean and Stark' conditions to remove residual water. Solvent (20.0 L) was removed by distillation at atmospheric pressure. n-Butanol (16.2 kg) was added. Solvent was removed in 10.0 L portions by distillation at atmospheric pressure, the volume being maintained by the addition of n-butanol in 10.0 L portions until 50.0 L of solvent had been removed and a solution temperature of 117° C. was attained. The solution was cooled to 10° C. and stirred at this temperature for 9 h and 5 min. The solution was filtered through a 1 micron filter. The filter and transfer lines were washed with n-butanol (3.7 kg) and the wash added to the balk.

The solution was heated to 65° C. and gaseous hydrogen chloride (1.5 kg, 41.14mol) was added over 5 min allowing the temperature to rise to 80° C. The mixture was heated to 0° C. to complete solution. the mixture was cooled to 20° C. over 3 h and 10 min, then to 5° C., and stirred at 5° C. for 1 h. The product was isolated by centrifugation, washed twice with ethyl acetate (1×17.8 kg, 1×13.4 kg), then dried in an atmospheric tray drier for 18 h at 50° C. to give a yield of 7.5 kg at 97.12% purity (7.28 kg at 100%).

EXAMPLE 14

3-{2-Thia-[(2- (E)-2-carboxyethenyl)-3-[8-(4-methoxyphenyl)octyloxy}-6-pyridyl]propylbenzoic Add n-Butyl-3-{6-hydroxymethyl-3-[8-(4-methoxyphenyl) octyloxy]pyridin-2-yl}-propenoate hydrochloride (4.0 kg, assumed to be 100%, 7.9 mol) was mixed with dichloromethane (24.6 kg). Thionyl chloride (2.66 kg, 22.4 mmol) was added over 15 min maintaining the temperature at 20°–25° C. The mixture was stirred at 20°–25° C. for 3 h. The organic solution was added over 15 min to a solution of sodium carbonate (4.0 kg at 99.28%, 3.97 kg at 100%, 37.46 mmol) in demineralised water (40.0 L). Dichloromethane (2.0 kg) was added and the mixture stirred for a further 10 min to give a pH of 7. The phases were allowed to separate for 14.5 h, and the organic phase removed. The aqueous phase was extracted with dichloromethane (10.6 kg) and discarded. The organic phase was washed with demineralised water (8.0 L), then with a solution of sodium chloride (2.5 kg) in demineralised water (8.0 L). Solvent (25.0 L) was removed by distillation at atmospheric pressure maintaining the temperature below 48° C. ('concentrate').

A solution of sodium hydroxide (1.98 kg, 49.5 mol) in demineralised water (4.6 L) was added m methanol (2.64 kg) maintaining the temperature at 20°–25° C. The mixture was stirred for 10 min, and methyl m-bromomethylbenzoate (1.54 kg, 8.5 mol) was added over 10 min. The mixture was stirred for 40 min to give complete solution ('sodium salt').

Tetrahydrofuran (7.4 kg) was added to the 'concentrate'. The 'sodium salt' solution was added over 1.25 h, maintaining the temperature at 25°–30° C. The mixture was stirred for 2 h and 35 min, then cooled to 15°–20° C. Hydrochloric acid (1M, 32.0 L) was added m the mixture over 1 hr and 5 min, maintaining the temperature at 15°–20° C., to give a pH of 4.5. The product precipitated as an oily solid. The mixture was stirred for 17 h. Demineralised water (30.0 L) was added to the mixture to convert the oily product to a crystalline material. The solid was isolated by filtration and washed with demineralised water (5.0 L).

The wet crude product was added to ethyl acetate (36.0 kg) and water was removed by distillation under 'Dean and Stark' conditions. Solvent was removed by distillation at atmospheric pressure, the volume being maintained by the addition of ethyl acetate in 4.0 L portions until 25.2 kg had been added. The mixture was stirred at reflux for 10 min to ensure complete solution.

The hot solution was filtered through a 1 micron filter, cooled to 20°–25° C. over 40 min, then stirred at this temperature for 1 hr and 5 min. The product was isolated by filtration and washed with ethyl acetate (4.5 kg) to give a wet weight of 5.5 kg. The product was dried in the vacuum tray drier at 50°–55° C. for 26 h to give a yield of 3.5 kg at 100% (78.5%).

We claim:

1. A process for the preparation of a compound of formula (I):

(I)

in which n is 1 to 20; $R^1$ is hydrogen, $C_{1-6}$alkyl or hydroxy$C_{1-6}$alkyl; and $R^2$ is hydrogen, $C_{1-6}$alkyl, $C_{1-6}$alkoxy or trifluoromethyl, which process comprises coupling a compound of formula (II):

(II)

in which n and $R^2$ are as defined in formula (I) and $R^3$ is halogen with a compound of formula (III):

(III)

in which $R^1$ is as defined in formula (I) in the presence of palladium catalyst.

2. A process for the preparation of a compound of formula (IA) or a salt or N-oxide thereof:

(IA)

in which: $R^1$ is hydrogen, benzyl or a group of formula (A):

(A)

where n is 1 to 20 and $R^5$ is hydrogen, $C_{1-6}$alkyl, $C_{1-6}$alkoxy or trifluoromethyl; m is 0 to 5;

$R^8$ and $R^9$ are independently hydrogen, halogen, $CO_2H$, $C_{1-6}$alkyl or $C_{1-6}$alkoxy; and $R^{10}$ is a group $CR^2{=}CR^3{-}R^4$ or $CHR^2{-}CHR^3{-}R^4$ where $R^2$ and $R^3$ are independently hydrogen or $C_{1-6}$alkyl and $R^4$ is cyano or $CO_2R^6$ where $R^6$ is hydrogen or $C_{1-6}$alkyl, which process comprises:

coupling a compound of formula (II):

(II)

in which $R^1$ is as defined in formula (IA) and $R^7$ is a leaving group with a compound of formula (III) or a salt thereof:

(III)

in which $R^2$, $R^3$ and $R^4$ are as defined in formula (IA)

in the presence of a palladium catalyst, to give a compound of formula (I):

(I)

in which $R^1$, $R^2$, $R^3$ and $R^4$ are as defined in formula (IA), and thereafter: converting the compound of formula (I) into a compound of formula (IA), or converting a compound of formula (IA) into another compound of formula (IA), or forming a pharmaceutically acceptable salt or N-oxide.

3. A process according to claim 1 in which the palladium coupling is carried out in aqueous DMF.

4. A process according to claim 3 in which $R^1$ is a group of formula (A) where n is 2 to 8.

5. A process according to claim to 4 in which $R^4$ is $CO_2R^6$ where $R^6$ is hydrogen or $C_{1-6}$alkyl.

6. A process according to claim 5 in which $R^5$ is methoxy.

7. A process according to claim 1 in which the compound prepared is: n-butyl 3-{6-hydroxymethyl-3-[8(4-methoxyphenyl)octyloxy]pyridin-2-yl}propenoate, methyl 3-[6-hydroxymethyl-3-[8(4-methoxyphenyl)octyloxy]pyridin-2-yl}propenoate, methyl 3-{6-hydroxymethyl-3-(phenylethyloxy)pyridin-2-yl}propenoate, t-butyl 3-{6-hydroxymethyl-3-[8(4-methoxyphenyl)octyloxy]pyridin-2-yl)propenoate, 3-{6-hydroxymethyl-3-[8(4-methoxyphenyl)octyloxy]pyridin-2-yl }propenoic acid, n-butyl 3-{6-hydroxymethyl-3-(phenylethyloxy)pyridin-2-yl}propenoate, ethyl (3-hydroxy-6-methylpyridin-2-yl)propenoate, ethyl 3-{3-hydroxy-6-hydroxymethylpyridin2-yl}propenoate, ethyl (3-benzyloxy-6-hydroxymethylpyridin-2-yl)propenoate, n-butyl (3-benzyloxy-6-hydroxymethylpyridin-2-yl)propenoate, methyl (3-benzyloxy-6-hydroxymethylpyridin-2-yl)propenoate, and and salts and N-oxides thereof.

8. A process according to claim 2 in which the compound of formula (IA) is 3[2-thia-3-[2-(E-2-carboxyethenyl-3-[8-(4-methoxyphenyl)octyloxy]-6-pyridyl]propyl]benzoic acid, [[1-thia-2-[6-(2-carboxyethyl)-5-phenylethyloxy-2-pyridyl]]ethyl]-2,6-dichlorobenzene, or [[1-thia-2-[6-(E-2-carboxyethenyl)-5-phenylethyloxy-2-pyridyl]]ethyl]-2,6-dichlorobenzene, or pharmaceutically acceptable salts or N-oxides thereof.

9. The process of claim 1 wherein the palladium catalyst is palladium (II) catalyst selected from the group consisting of $Pd(OAc)_2$, $Pd(OAc)_2/(o\text{-}tol)_3P$, $Pd(OAc)_2/$ $Ph_3P$, $Pd(OAc)_2/tri(2\text{-}furyl)phosphine$, $(Ph_3P)_2PdCl_2$, and $PdCl_2/Ph_3P$.

10. The process according to claim 9 wherein the catalyst is bis(triphenylphosphine)palladium dichloride or palladium acetate.

11. The process of claim 2 wherein the palladium catalyst is a palladium (II) catalyst selected from the group consisting of $Pd(OAc)_2$, $Pd(OAc)_2/(o\text{-tol})_3P$, $Pd(OAc)_2/Ph_3P$, $Pd(OAc)_2/tri(2\text{-furyl})phosphine$, $(Ph_3P)_2PdCl_2$, and $PdCl_2/Ph_3P$.

12. The process according to claim 11 wherein the catalyst is bis(triphenylphosphine)palladium dichloride.

* * * * *